(12) United States Patent
Hung et al.

(10) Patent No.: US 9,561,275 B2
(45) Date of Patent: Feb. 7, 2017

(54) COMPOSITIONS AND METHODS FOR RENDERING TUMOR CELLS SUSCEPTIBLE TO CD8+ T CELL-MEDIATED KILLING

(71) Applicant: THE JOHNS HOPKINS UNIVERSITY, Baltimore, MD (US)

(72) Inventors: Chien-Fu Hung, Timonium, MD (US); T. C. Wu, Stevenson, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/427,847

(22) PCT Filed: Sep. 13, 2013

(86) PCT No.: PCT/US2013/059744
§ 371 (c)(1),
(2) Date: Mar. 12, 2015

(87) PCT Pub. No.: WO2014/043523
PCT Pub. Date: Mar. 20, 2014

(65) Prior Publication Data
US 2015/0231239 A1 Aug. 20, 2015

Related U.S. Application Data

(60) Provisional application No. 61/701,094, filed on Sep. 14, 2012.

(51) Int. Cl.
| | | |
|---|---|---|
| A61K 39/00 | (2006.01) | |
| A61K 39/395 | (2006.01) | |
| C12P 21/08 | (2006.01) | |
| C07K 16/00 | (2006.01) | |
| A61K 31/7088 | (2006.01) | |
| C07K 16/30 | (2006.01) | |
| C07K 7/06 | (2006.01) | |
| C07K 5/11 | (2006.01) | |
| A61K 38/07 | (2006.01) | |
| A61K 48/00 | (2006.01) | |

(52) U.S. Cl.
CPC ..... *A61K 39/39558* (2013.01); *A61K 31/7088* (2013.01); *A61K 38/07* (2013.01); *A61K 39/0005* (2013.01); *A61K 48/00* (2013.01); *C07K 5/1019* (2013.01); *C07K 7/06* (2013.01); *C07K 16/30* (2013.01); *A61K 2039/505* (2013.01); *A61K 2039/585* (2013.01); *A61K 2039/6056* (2013.01); *A61K 2039/627* (2013.01); *C07K 2317/622* (2013.01); *C07K 2319/30* (2013.01); *C07K 2319/33* (2013.01); *C07K 2319/50* (2013.01)

(58) Field of Classification Search
None
See application file for complete search history.

(56) References Cited

U.S. PATENT DOCUMENTS

| 7,368,110 B2 * | 5/2008 | Pastan | A61K 47/48484 424/133.1 |
|---|---|---|---|
| 7,842,480 B2 * | 11/2010 | Celis | C07K 14/4748 435/69.7 |
| 2012/0189644 A1 | 7/2012 | Kahnert et al. | |

FOREIGN PATENT DOCUMENTS

| EP | 2256134 A1 | 12/2010 |
|---|---|---|
| WO | 02-094994 A2 | 11/2002 |
| WO | 2009-059309 A2 | 5/2009 |
| WO | 2011-020783 A2 | 2/2011 |

OTHER PUBLICATIONS

Kang, T., et al. "Targeted coating with antigenic peptide renders tumor cells susceptible to CD8+ T cell-mediated killing" Molecular Therapy, Mar. 2013, vol. 21, No. 3, pp. 542-553.

* cited by examiner

*Primary Examiner* — Shulamith H Shafer
(74) *Attorney, Agent, or Firm* — John Hopkins Technology Transfer

(57) ABSTRACT

The present invention provides an immunoconjugate having the formula: T-c-$E_n$-c-$Fc_n$ or T-c-$Fc_n$-c-$E_n$; wherein, T is a single chain variable portion fragment of a monoclonal antibody (scFv) directed to a target protein, polypeptide, or fragment thereof, which is highly expressed on cancer cells; E is two or more foreign immunogenic CD8$^+$ T cell antigenic epitopes; c is a peptide or polypeptide fragment thereof, capable of being cleaved by a specific protease; and Fc is two or more Fc portions of an IgG antibody. Nucleic acid sequences encoding the same and vectors containing said nucleic acid sequences are also provided. Methods of making the immunoconjugate, along with methods of making target cells susceptible to CTL mediated cell killing, and methods for treatment of cancers are also provided.

5 Claims, 14 Drawing Sheets

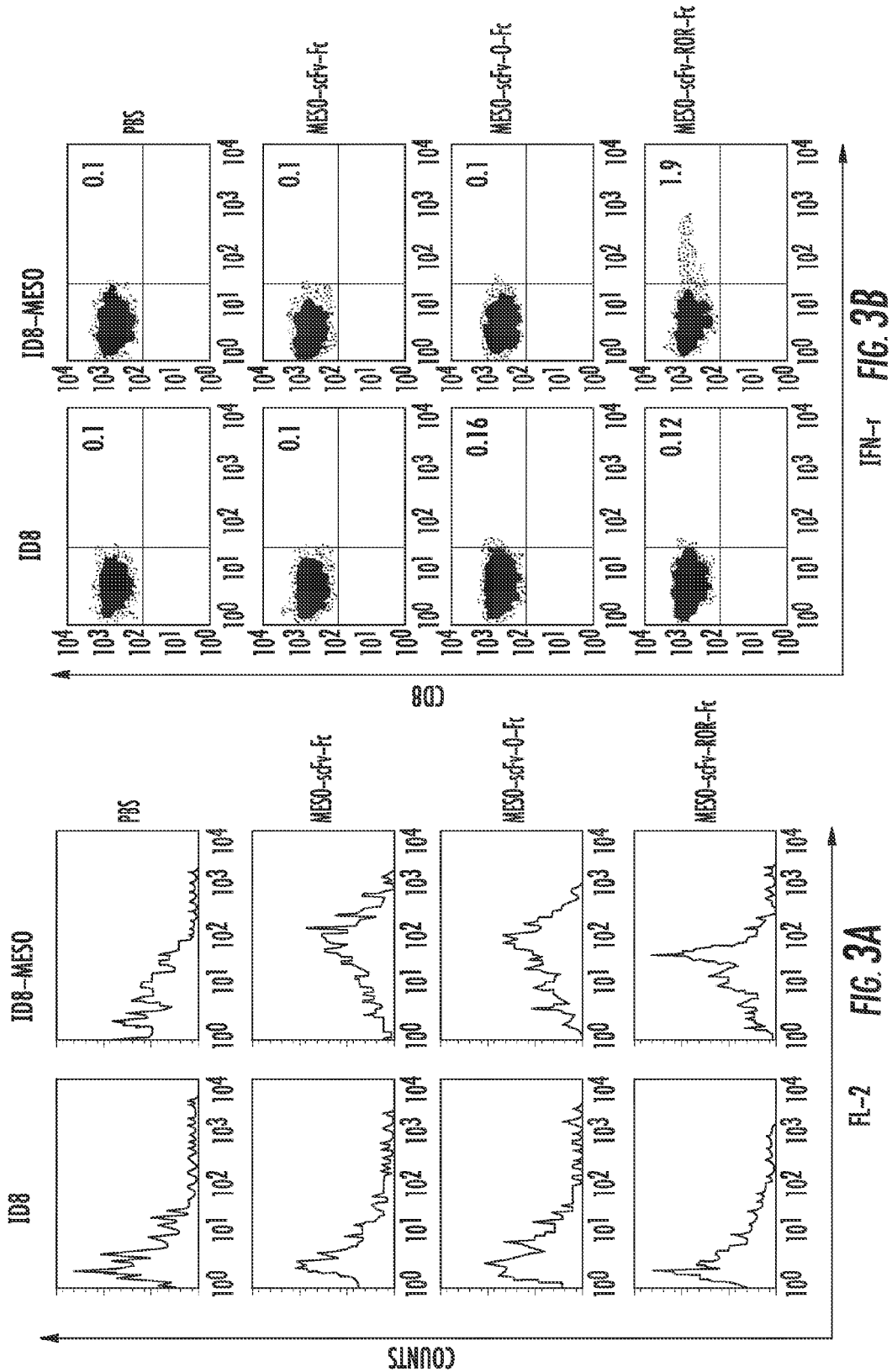

COMPOSITIONS AND METHODS FOR RENDERING TUMOR CELLS SUSCEPTIBLE TO CD8+ T CELL-MEDIATED KILLING

CROSS-REFERENCE TO RELATED APPLICATIONS

This application is a 35 U.S.C. §371 U.S. national entry of International Application PCT/US2013/059744, having an international filing date of Sep. 13, 2013, which claims the benefit of U.S. Provisional Patent Application No. 61/701,094, filed on Sep. 14, 2012, the content of each of the aforementioned applications is herein incorporated by reference in their entirety.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Aug. 9, 2016, is named P11613-04_ST25.txt and is 731 bytes in size.

BACKGROUND OF THE INVENTION

Antigen-specific immunotherapy is important for its ability to harness the immune system to specifically target tumors without the toxicity associated with traditional chemoradiation. Cytotoxic CD8+ T lymphocytes (CTLs) can selectively kill tumor cells at multiple sites throughout the body. Furthermore, antigen-specific immunotherapy is unlikely to generate non-specific autoimmunity. However, antigen-specific immunotherapy targeting tumor-associated endogenous antigen faces the major obstacle of immune tolerance.

A need continues to exist for novel modes of immunotherapy which can effectively target specific cancers without stimulating the tolerance mechanisms of the patient's immune system.

SUMMARY OF THE INVENTION

In accordance with an embodiment, the present invention provides an immunoconjugate having the formula:

$$T\text{-}c\text{-}E_n\text{-}c\text{-}Fc_n;$$

wherein, T is a single chain variable portion fragment of a monoclonal antibody (scFv) directed to a target protein, polypeptide, or fragment thereof, which is highly expressed on cancer cells; E is one or more foreign immunogenic CD8+ T cell antigenic epitopes and n is 1 to 10; c is a peptide or polypeptide fragment thereof, capable of being cleaved by a specific protease; and $Fc_n$ is at least two or more Fc portions of an IgG antibody wherein n is 1 to 10.

In accordance with another embodiment, the present invention provides an immunoconjugate having the formula:

$$T\text{-}c\text{-}E_n\text{-}c\text{-}Fc_n;$$

wherein, T is a single chain variable portion fragment of a monoclonal antibody (scFv) directed to mesothelins; E is at least two foreign immunogenic CD8+ T cell antigenic epitopes of ovalbumin; c is a peptide having the amino acid sequence RVKR (SEQ ID NO: 2), capable of being cleaved by furin; and Fc is at least two Fc portions of the IgG2a protein.

In accordance with another embodiment, the present invention provides an immunoconjugate having the formula:

$$T\text{-}c\text{-}Fc_n\text{-}c\text{-}E_n;$$

wherein, T is a single chain variable portion fragment of a monoclonal antibody (scFv) directed to a target protein, polypeptide, or fragment thereof, which is highly expressed on cancer cells; E is one or more foreign immunogenic CD8+ T cell antigenic epitopes and wherein n is 1 to 10; c is a peptide or polypeptide fragment thereof, capable of being cleaved by a specific protease; and $Fc_n$ is at least two or more Fc portions of an IgG antibody wherein n is 1 to 10.

In accordance with yet another embodiment, the present invention provides a nucleic acid molecule which encodes the immunoconjugates described above.

In accordance with still a further embodiment, the present invention provides a plasmid which comprises a nucleic acid molecule which encodes the immunoconjugates described above.

In accordance with an embodiment, the present invention provides a method for making a tumor cell susceptible to CD8+ T cell killing, comprising contacting one or more tumor cells with the immunoconjugate described above.

In accordance with another embodiment, the present invention provides a method for making a tumor cell susceptible to CD8+ T cell killing, comprising transfecting one or more tumor cells with the nucleic acid molecule or the plasmid or vector described above.

In accordance with a further embodiment, the present invention provides a method for treating cancer in a subject, comprising administering to the subject, a therapeutically effective amount of the immunoconjugate described above and a pharmaceutically acceptable carrier.

In accordance with still another embodiment, the present invention provides a method for treating cancer in a subject, comprising administering to the subject, a therapeutically effective amount of the immunoconjugate described above, at least one or more therapeutic agents, and a pharmaceutically acceptable carrier.

BRIEF DESCRIPTION OF THE DRAWINGS

FIGS. 3A-3C depict MHC class I presentation of OVA peptide to OVA-specific CD8+ T cells by ID8-meso cells treated with Meso-scFv-ROR-Fc in vivo. 3A is flow cytometry characterization of Meso-scFv-ROR-Fc immunoconjugate binding to ID8-meso tumor cells. Mice were i.p. injected with GFP-expressing ID8-meso or control IDB tumor cells followed by i.p injection of different Meso-scFv-Fc immunoconjugates. Tumor cells isolated from peritoneal wash of treated tumor-bearing mice were stained with PE-labeled anti-mouse Fc antibody and analyzed by flow cytometry analysis. GFP-positive cells were gated for analysis. 3B is the flow cytometry characterization of OVA-specific CD8+ T cell activation by tumor cells treated with different immunoconjugates. Tumor cells from peritoneal wash of tumor-bearing mice treated with different immunoconjugates were incubated with OVA-specific CD8+ T cells. OVA-specific CD8+ T cell activation was determined by CD8 and intracellular IFN-γ staining. 3C is a representative bar graph depicting % of IFN-γ-secreting OVA-specific CD8+ T cells out of total OVA-specific T cells (mean±S.D.).

DETAILED DESCRIPTION OF THE INVENTION

Figures 1A, 1B:
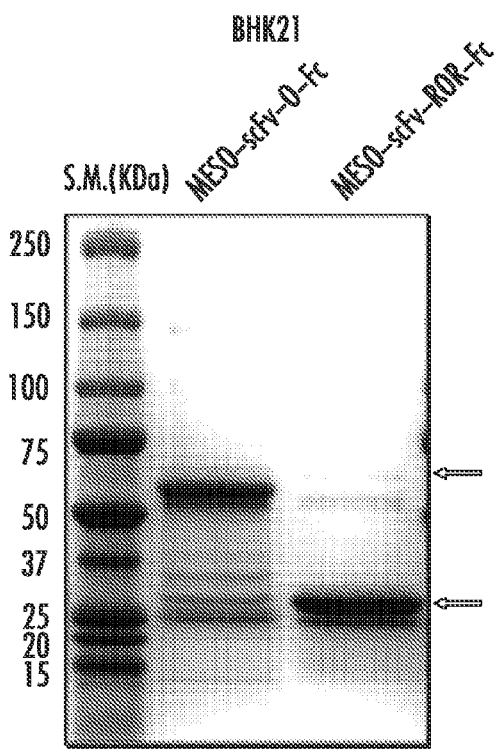
FIGS. 1A-1D depict the generation and characterization of an embodiment of the therapeutic chimeric proteins (immunoconjugates) of the present invention. 1A is a schematic diagram of different immunoconjugates (Meso-scFv-Fc) containing anti-human mesothelin single chain variable fragment (Meso-scFv), OVA peptide (SIINFEKL) (SEQ ID NO: 1), furin cleavage sites (RVKR) (SEQ ID NO: 2), and Fc protein (IgG2a). 1B & 1C depict gel electrophoresis of isolated proteins from (B) furin-positive BHK21 cells or (C) furin-deficient FD11 cells transfected with the different types of Meso-scFv-Fc. Protein was isolated from supernatant of cultured cells then characterized by SDS-PAGE and coomassie Brilliant Blue staining. 1D shows representative flow cytometry analysis of immunoconjugate bound to ID8-meso with ID8 cells as the control. ID8-meso was generated through transfection of ID8 cells with DNA encoding human mesothelin as previously described. Purified proteins were incubated with either ID8-meso or ID8 cells then stained with PE-labeled anti-mouse Fc antibody.

In accordance with one or more embodiments, the present invention provides an innovative approach for bypassing immune tolerance by using pre-existing immunity against a foreign immunogenic CD8+ T cell antigenic epitopes. Most individuals have T cell-mediated immunity against many common viral infections such as Epstein-Barr virus, human cytomegalovirus, and influenza. Additionally, many MHC class I-restricted immunogenic CTL epitopes have been identified for these common viral infections. By introducing multiple foreign viral CTL antigenic peptides to coat tumor cells, the compositions and methods of the present invention can potentially exploit the preexisting viral antigen-specific CTLs found in most individuals and direct these cells to target the tumor.

In accordance with an embodiment, the present invention provides an immunoconjugate having the formula:

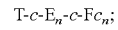

wherein, T is a single chain variable portion fragment of a monoclonal antibody (scFv) directed to a target protein, polypeptide, or fragment thereof, which is highly expressed on cancer cells; E is one or more foreign immunogenic CD8+ T cell antigenic epitopes and n is 1 to 10; c is a peptide or polypeptide fragment thereof, capable of being cleaved by a specific protease; and $Fc_n$ is at least two or more Fc portions of an IgG antibody wherein n is 1 to 10.

As used herein, the term "immunoconjugate" is a conjugate of a binding molecule (e.g., an antibody) with an atom, molecule, or a higher-ordered structure (e.g., with a liposome), and an antigen, and/or therapeutic agent, and/or a diagnostic agent.

The term "cancer antigen" or "antigenic epitope" as used herein refers to any molecule (e.g., protein, peptide, lipid, carbohydrate, etc.) solely or predominantly expressed or over-expressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host.

As used herein, the term "E" and/or "foreign immunogenic CD8+ T cell antigenic epitope" means an MHC class I-restricted foreign immunogenic CTL epitope which allows CD8+ T cells within the context of the immunity of the subject, to recognize the peptide. Examples of such peptides include, but are not limited to, OVA peptide (SIINFEKL) (SEQ ID NO: 1), Influenza A PB1, Influenza A NP, EBV BMLF1, Influenza A Matrix 1, HCMV pp65, EBV BRLF1, EBV EBNA3A, EBV EBNA3B, EBV BZLF1, and EBV EBNA3C.

The term "polypeptide" as used herein includes oligopeptides and refers to a single chain of amino acids connected by one or more peptide bonds.

The term "a peptide or polypeptide fragment thereof, capable of being cleaved by a specific protease" as used herein, means an amino acid sequence which is specifically recognized by a protease enzyme and specifically binds and hydrolytically cleaves that amino acid sequence. The peptide sequence can be any sequence of between about 3 to about 20 amino acids in length, which is known to be cleaved by a known protease. In one or more embodiments, the present invention provides an immunoconjugate where the peptide or polypeptide fragment thereof, capable of being cleaved by a specific protease is an amino acid sequence cleaved by a protease normally found on cancer cell membranes. Preferably, the protease is furin, which is found on many types of tumor cells.

The term "functional portion" when used in reference to a monoclonal antibody or antigenic epitope refers to any part or fragment, which part or fragment retains the biological activity of which it is a part (the parent molecule, antibody, or antigen). Functional portions encompass, for example, those parts that retain the ability to specifically bind to the antigen (e.g., in an MHC-independent manner), or detect, treat, or prevent the disease, to a similar extent, the same extent, or to a higher extent, as the parent molecule. In reference to the parent molecule, the functional portion can comprise, for instance, about 10%, 25%, 30%, 50%, 68%, 80%, 90%, 95%, or more, of the parent molecule.

The functional portion can comprise additional amino acids at the amino or carboxy terminus of the portion, or at both termini, which additional amino acids are not found in the amino acid sequence of the parent molecule. Desirably, the additional amino acids do not interfere with the biological function of the functional portion, e.g., specifically binding to a cancer antigen, having the ability to detect cancer, treat or prevent cancer, etc. More desirably, the additional amino acids enhance the biological activity, as compared to the biological activity of the parent molecule.

By "protein" is meant a molecule comprising one or more polypeptide chains.

In this regard, the invention also provides an immunoconjugate molecule comprising at least one of the polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof. Suitable methods of making fusion proteins are known in the art, and include, for example, recombinant methods. See, for instance, Choi et al., *Mol. Biotechnol.* 31: 193-202 (2005).

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

In accordance with another embodiment, the present invention provides an immunoconjugate having the formula:

$$T\text{-}c\text{-}E_n\text{-}c\text{-}Fc_n;$$

wherein, T is a single chain variable portion fragment of a monoclonal antibody (scFv) directed to mesothelins; E is at least two foreign immunogenic CD8+ T cell antigenic epitopes of ovalbumin; c is a peptide having the amino acid sequence RVKR (SEQ ID NO: 2), capable of being cleaved by furin; and Fc is at least two Fc portions of the IgG2a protein. In accordance with another embodiment, peptide portion, c, of the immunoconjugate can comprise a cleavage sequence from matrix metalloproteases, such as MMP2 and/or MMP9.

In accordance with an embodiment, the scFv portion of the immunoconjugate can be directed to other well-known proteins highly expressed on cancer or other target cells when compared to normal cells in the body. Examples of such proteins include, without limitation, epidermal growth factor receptor (EGFR) proteins, Her2/neu and others known in the art.

Included in the scope of the invention are functional variants of the inventive immunoconjugate, and polypeptides, and proteins described herein. The term "functional variant" as used herein refers to an immunoconjugate, polypeptide, or protein having substantial or significant sequence identity or similarity to a parent immunoconjugate, polypeptide, or protein, which functional variant retains the biological activity of the immunoconjugate, polypeptide, or protein of which it is a variant. In reference to the parent immunoconjugate, polypeptide, or protein, the functional variant can, for instance, be at least about 30%, 50%, 75%, 80%, 90%, 98% or more identical in amino acid sequence to the parent immunoconjugate, polypeptide, or protein.

The functional variant can, for example, comprise the amino acid sequence of the parent immunoconjugate, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc Alternatively or additionally, the functional variants can comprise the amino acid sequence of the parent immunoconjugate, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent immunoconjugate, polypeptide, or protein.

The immunoconjugate, polypeptide, and/or protein of the invention (including functional portions and functional variants thereof) can be obtained by methods known in the art. Suitable methods of de novo synthesizing polypeptides and proteins are described in references, such as Chan et al., Fmoc Solid Phase Peptide Synthesis, Oxford University Press, Oxford, United Kingdom, 2005; Peptide and Protein Drug Analysis, ed. Reid, R., Marcel Dekker, Inc., 2000; Epitope Mapping, ed. Westwoood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, NY, 1994. Further, some of the immunoconjugates, polypeptides, and proteins of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the immunoconjugates, polypeptides, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive immunoconjugates, polypeptides, and proteins can be synthetic, recombinant, isolated, and/or purified.

In accordance with yet another embodiment, the present invention provides a nucleic acid molecule which encodes the immunoconjugates described above.

Further provided by the invention is a nucleic acid comprising a nucleotide sequence encoding any of the immunoconjugates, polypeptides, or proteins described herein (including functional portions and functional variants thereof).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

In some embodiments, the substituted nucleic acid sequence may be optimized. Without being bound to a particular theory, it is believed that optimization of the nucleic acid sequence increases the translation efficiency of the mRNA transcripts. Optimization of the nucleic acid sequence may involve substituting a native codon for another codon that encodes the same amino acid, but can be translated by tRNA that is more readily available within a cell, thus increasing translation efficiency. Optimization of the nucleic acid sequence may also reduce secondary mRNA structures that would interfere with translation, thus increasing translation efficiency.

The invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

In accordance with still a further embodiment, the present invention provides a plasmid which comprises a nucleic acid molecule which encodes the immunoconjugates described above.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages do not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the immunoconjugate, polypeptide, or protein (including functional portions and functional variants thereof), or to the nucleotide sequence which is complementary to or which hybridizes to the nucleotide sequence encoding the immunoconjugate, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The antibody or fragments thereof used in the immunoconjugates of the present invention, can be any type of immunoglobulin that is known in the art. For instance, the antibody or fragments thereof can be of any isotype, e.g., IgA, IgD, IgE, IgG, IgM, etc. The antibody can be monoclonal or polyclonal. The antibody or fragments thereof, can be a naturally-occurring antibody, e.g., an antibody isolated and/or purified from a mammal, e.g., mouse, rabbit, goat, horse, chicken, hamster, human, etc. Alternatively, the antibody or fragments thereof can be a genetically-engineered antibody, e.g., a humanized antibody or a chimeric antibody. The antibody can be in monomeric or polymeric form. Also, the antibody or fragments thereof can have any level of affinity or avidity for the target cell or population of cell antigen(s). Desirably, the antibody is specific for the functional portion of the target cell or population of cells, such that there is minimal cross-reaction with other cells or populations of cells.

Suitable methods of making antibodies are known in the art. For instance, standard hybridoma methods are described in, e.g., Köhler and Milstein, Eur. J. Immunol., 5, 511-519 (1976), Harlow and Lane (eds.), Antibodies: A Laboratory Manual, CSH Press (1988), and C. A. Janeway et al. (eds.), Immunobiology, 5th Ed., Garland Publishing, New York, N.Y. (2001)). Alternatively, other methods, such as EBV-hybridoma methods (Haskard and Archer, J. Immunol. Methods, 74(2), 361-67 (1984), and Roder et al., Methods Enzymol., 121, 140-67 (1986)), and bacteriophage vector expression systems (see, e.g., Huse et al., Science, 246, 1275-81 (1989)) are known in the art.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. Mol. Biol., 235, 959-973 (1994).

The invention also provides antigen binding portions of any of the antibodies described herein. The antigen binding portion can be any portion that has at least one antigen binding site, such as Fab, F(ab')2, dsFv, sFv, diabodies, and triabodies.

A single-chain variable region fragment (scFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., Protein Engineering, 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

In accordance with a further embodiment, the present invention provides a method for treating cancer in a subject, comprising administering to the subject, a therapeutically effective amount of the immunoconjugate described above and a pharmaceutically acceptable carrier.

The immunoconjugates of the present invention can be formulated into a composition, such as a pharmaceutical composition. In this regard, the invention provides a pharmaceutical composition comprising any of the immunoconjugates, polypeptides, proteins, functional portions, functional variants, nucleic acids, expression vectors, and a pharmaceutically acceptable carrier. The inventive pharmaceutical compositions containing any of the inventive immunoconjugates can comprise more than one immunoconjugate.

In accordance with still another embodiment, the present invention provides a method for treating cancer in a subject, comprising administering to the subject, a therapeutically effective amount of the immunoconjugate described above, at least one or more therapeutic agents, and a pharmaceutically acceptable carrier.

Examples of therapeutically active agents or drugs, such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular immunoconjugate, as well as by the particular method used to administer the immunoconjugate. Accordingly, there are a variety of suitable formulations of the pharmaceutical composition of the invention. The following formulations for oral, aerosol, parenteral, subcutaneous, intravenous, intramuscular, intraarterial, intrathecal, interperitoneal, rectal, and vaginal administration are exemplary and are in no way limiting. More than one route can be used to administer the immunoconjugate, and in certain instances, a particular route can provide a more immediate and more effective response than another route.

Formulations suitable for oral administration can consist of (a) liquid solutions, such as an effective amount of the immunoconjugate dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the immunoconjugate in a flavor, usually sucrose and acacia or tragacanth, as well as pastilles comprising the immunoconjugate in an inert base, such as gelatin and glycerin, or sucrose and acacia, emulsions, gels, and the like containing, in addition to, such excipients as are known in the art.

Injectable formulations are in accordance with the invention. The requirements for effective pharmaceutical carriers for injectable compositions are well-known to those of ordinary skill in the art (see, e.g., Pharmaceutics and Pharmacy Practice, J. B. Lippincott Company, Philadelphia, Pa., Banker and Chalmers, eds., pages 238-250 (1982), and ASHP Handbook on Injectable Drugs, Toissel, 4th ed., pages 622-630 (1986)). Preferably, when administering cells, e.g., dendritic cells, the cells are administered via injection.

It will be appreciated by one of skill in the art that, in addition to the above-described pharmaceutical compositions, the immunoconjugate of the invention can be formulated as inclusion complexes, such as cyclodextrin inclusion complexes, or liposomes.

For purposes of the invention, the amount or dose of the immunoconjugate administered should be sufficient to effect, e.g., a therapeutic or prophylactic response, in the subject or animal over a reasonable time frame. For example, the dose of the immunoconjugate should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular immunoconjugate and the condition of the animal (e.g., human), as well as the body weight of the animal (e.g., human) to be treated.

In accordance with an embodiment, the present invention provides a composition comprising a therapeutically effective amount of the immunoconjugates described herein, or the nucleic acid molecules described herein, or the plasmid or the vector described herein, and a pharmaceutically acceptable carrier for use in a medicament, preferably for use in the treatment cancer in a subject. In another embodiment the composition described above can include at least one or more additional therapeutic agents.

Specific examples of useful therapeutic agents can include anti-neoplastics such as androgen inhibitors, antimetabolites, cytotoxic agents, and immunomodulators. Further examples of antineoplastic agents include alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

In accordance with an embodiment, the present invention provides a method for making a tumor cell susceptible to $CD8^+$ T cell killing, comprising contacting one or more tumor cells with the immunoconjugate described above.

In one or more embodiments, the tumor cells are cancer tumor cells. With respect to the inventive immunoconjugates and methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, gastrointestinal carcinoid tumor. Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer. Preferably, the cancer is ovarian cancer.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

EXAMPLES

Mice. Female C57BL/6 mice (6-8 weeks old) were purchased from National Cancer Institute (Frederick, Md.). All animal procedures were performed according to approved protocols and in accordance with recommendations for the proper use and care of laboratory animals.

Luciferase-expressing syngeneic mouse ovarian epithelial cancer cell lines, ID8 and ID8-meso, have been described previously (Gene Therapy 14: 1189-119 (2007). Luciferase-expressing TC-1 and TC-1-meso cells were generated by same methods described above. BHK (baby hamster kidney) 21 cells were also obtained from the ATCC (Rockville, Md.). The generation of OVA-specific T cell line has been described previously (Gene Therapy 17: 1453-1464 (2010)). FD11 (a furin-deficient CHO cell line) has been well characterized, and was kindly provided by Dr Stephen H. Leppla at National Institutes of Health.

For purification of the various anti-human mesothelin scFv fragments, 50 ug of plasmid was transfected into $1\times10^7$ furin-deficient FD11 cells in T-150 flask using Lipofectamine 2000 (Invitrogen Corp., Carlsbad, Calif., USA). After 3 days, cell cultured media was accumulated, filtered using 0.22 μm syringe filter (Millipore, Billerica, Mass., USA) and concentrated with Amicon cut-off 50 kDa Ultra-15 (Millipore, Billerica, Mass., USA). Concentrated recombinant protein containing media was applied to a HiTrap Protein G HP column (GE Healthcare) and followed vendor's protocol. Protein concentrations were determined by the Coomassie Plus protein assay (Pierce, Rockford, USA) and purity was estimated by SDS polyacrylamide gel electrophoresis.

For flow cytometry analysis, tumor cells were stained with 0.5 μg purified the various anti-human mesothelin scFv fragments respectively and PE-conjugated anti-mouse antibody was used as a detection antibody (BD Bioscience). Percentage of OVA-specific IFN-γ-secreting $CD8^+$ T cells was determined using intracellular cytokine staining and FACScan analysis with CELLQuest software (Becton Dickinson Immunocytometry System, Mountain View, USA). For immunofluorescence staining, cells were stained with each protein, followed by PE conjugated anti-mouse Fc antibody after incubation for 0 minutes or 60 minutes at 37° C. Stained cells were examined using fluorescence microscopy (Carl Zeiss, Oberkochen, Germany).

For T cell activation, tumor cells were added to 48-well plates at a dose of $1\times10^5$ cells/well and incubated with different concentrations of proteins. Eighteen hours later, treated tumor cells were incubated with $2\times10^5$ OVA-specific cytotoxic T cells (CTL). One day after activation, IFN-γ-secreting OVA specific $CD8^+$ T cells were identified by intracellular cytokine staining and analyzed by flow cytometry analysis. For in vitro cytotoxicity experiment, $1\times10^5$ of luciferase-expressing tumor cells were stained with each different protein on 24-well plate during 18 hours and treated with 2×10$^5$ OVA-specific cytotoxic T cells. The degree of CTL-mediated killing of the tumor cells was measured by the IVIS luminescence imaging system series 2000. Bioluminescence signals were acquired for 1 minute.

For cell-specific binding experiment, 1×10$^6$ GFP-expressing ID8 or ID8-meso cells were injected into C57BL/6 mice (3 per group) using intraperitoneal injection. After 24 hours, mice were each injected intraperitoneally with 10 ug scFv protein followed by intraperitoneal wash after 18 hours. Intraperitoneally washed cells were stained with PE-conjugated anti-mouse Fc antibody and analyzed by flow cytometry. For T cell activation, 1×10$^6$ intraperitoneally washed cells of each group were incubated with 1×10$^5$ OVA-specific T cells and activated IFN-γ-secreting OVA specific CD8$^+$ T cells were analyzed by flow cytometry analysis.

For in vivo tumor treatment experiments, 1×10$^5$ luciferase-expressing ID8-meso cells were injected into C57BL/6 mice (5 per group) using intraperitoneal injection. After 10 days, 20 μg of each scFv-protein was injected with or without 5×10$^6$ OVA T cell using intraperitoneal injection. Fluorescence intensity in tumor bearing mice treated with each scFv-protein was measured by the IVIS luminescence imaging system series 2000.

The data presented in this study are representative of at least two experiments performed, and are expressed as means±standard deviation (S.D.). The number of samples in each group for any given experiment was >3. Results for intracellular cytokine staining with flow cytometry analysis and tumor treatment experiments were evaluated by analysis of variance (one-way ANOVA) and the Tukey-Kramer multiple comparison test. Comparisons between individual data points were performed using Students' t-test. The event time distributions for different mice were compared using the Kaplan and Meier method and the log-rank statistic. All p values<0.05 were considered significant.

Example 1

Figure 1C:
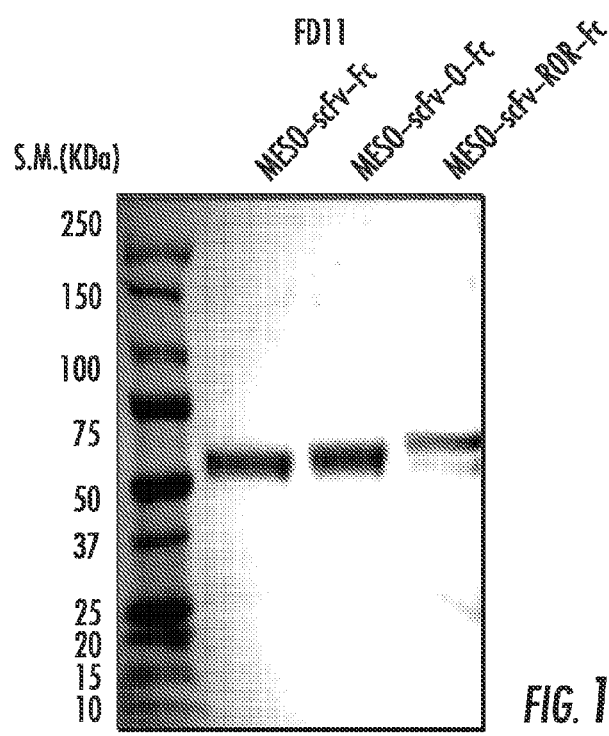

An immunoconjugate comprising an anti-human mesothelin single chain variable fragment (Meso-scFv) conjugated with Fc (IgG2a) protein containing OVA peptide flanked with furin cleavage sites (Meso-scFv-ROR-Fc was created. FIG. 1A is the schematic diagram of immunoconjugate Meso-scFv-ROR-Fc construct, control Meso-scFv-Fc protein without OVA peptide, and control Meso-scFv-O-Fc protein without furin cleavage sites. As shown in FIG. 1B, only the furin-expressing BHK21 cells transfected with Meso-scFv-ROR-Fc had a 30 kDA band that is consistent with the size of Fc fragment, suggesting cleavage of the chimeric Meso-scFv-ROR-Fc. In comparison, BHK21 cells transfected with Meso-scFv-O had a 60 kDa band that is consistent with the size of uncleaved full length protein. In addition, furin-deficient FD11 cells were transfected with various Meso-scFv-Fc immunoconjugates. As shown in FIG. 1C, the FD11 cells transfected with Meso-scFv-ROR-Fc showed an approximately 60 kDA band that is consistent with the size of uncleaved, full length protein. These results indicate furin expressed by cancers can act on the furin cleavage sites of the Meso-scFv-ROR-Fc immunoconjugate.

Example 2

Figure 1D:
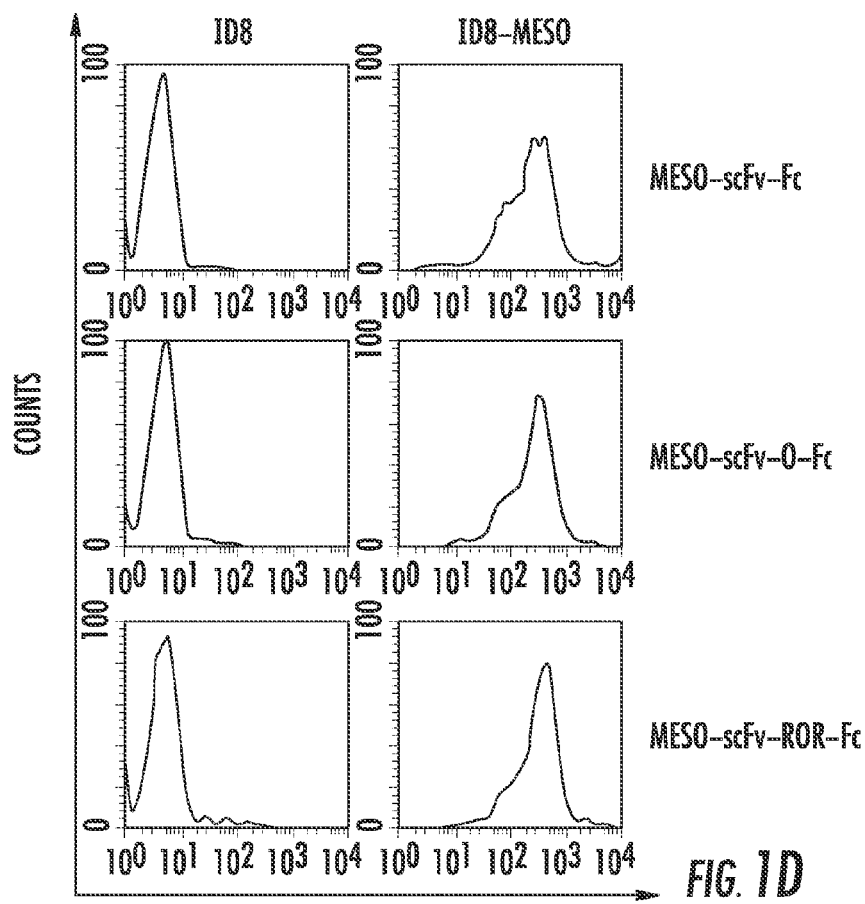

To determine whether various Meso-scFv-Fc immunoconjugates can selectively bind to human mesothelin-expressing murine ovarian tumor cell line, ID8-meso, flow cytometry analysis was performed. As shown in FIG. 1D, human mesothelin-expressing ID8-meso cells incubated with various Meso-scFv-Fc immunoconjugates displayed a shift consistent with more cell binding compared to non mesothelin-expressing ID8 cells, which suggests meso-scFv-Fc immunoconjugate binds specifically to human mesothelin-expressing ID8-meso tumor cells.

Example 3

It was then determined if the binding of Meso-scFv-ROR-Fc to human mesothelin-expressing ID8-meso could facilitate the cleavage of furin recognition sites in the immunoconjugate. ID8-meso or control ID8 tumor cells were incubated with the immunoconjugate Meso-scFv-Fc or Meso-scFv-ROR-Fc then stained with PE-labeled anti-mouse Fc antibody before visualization by fluorescence microscopy. ID8-meso incubated with Meso-scFv-ROR-Fc or Meso-scFv-Fc immunoconjugate had similar levels of red fluorescent activity at 0 minutes (data not shown). However, the red fluorescent activity of ID8-meso incubated with Meso-scFv-ROR-Fc was greatly reduced at 60 minutes. The results indicate that furin-mediated proteolysis of the Meso-scFv-ROR-Fc immunoconjugate cleavage sites results in the loss of Fc fragment (reduced fluorescence, data not shown).

Example 4

Figure 2A:
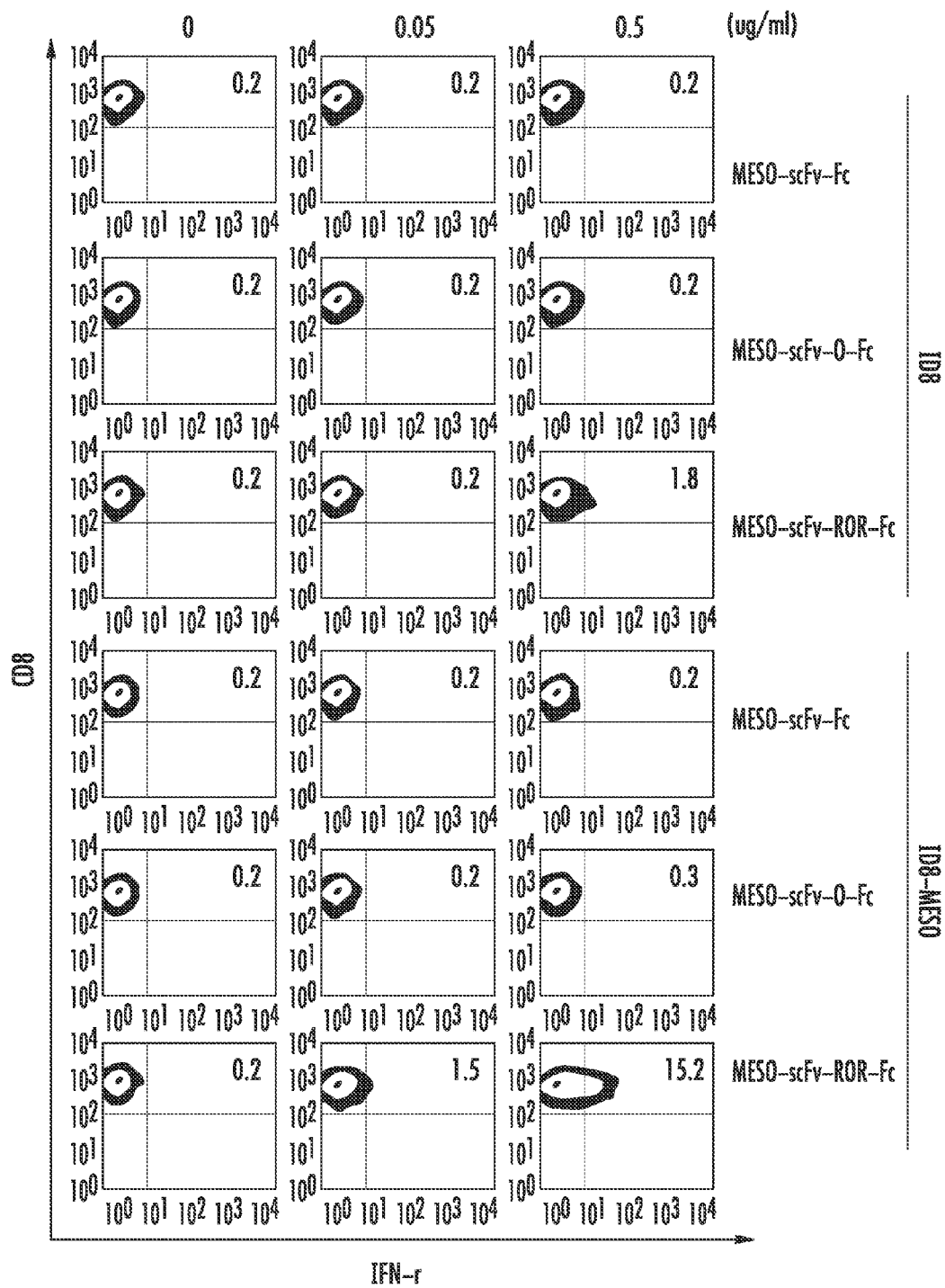
FIGS. 2A-2D depict MHC class I presentation of OVA peptide to OVA-specific CD8+ T cells by ID8-meso cells treated with Meso-scFv-ROR-Fc. 2A shows flow cytometry characterization of OVA-specific CD8+ T cell activation by ID8-meso cells treated with different immunoconjugates of the present invention. ID8-meso or control ID8 tumor cells were incubated with different protein concentrations followed by incubation with 2×10⁵ OVA-specific cytotoxic T cells (CTLs). OVA-specific CD8+ T cell activation was determined by CD8 and intracellular IFN-γ staining. 2B shows a representative bar graph depicting the % of IFN-γ-secreting OVA-specific CD8+ T cells out of total OVA-specific T cells (mean±S.D.). 2C is representative luminescence imaging of in vitro OVA-specific CTL killing of luciferase-expressing ID8-meso cells treated with different concentrations of the Meso-scFv-ROR-Fc immunoconjugate. Luciferase-expressing ID8-meso or control ID8 tumor cells treated with immunoconjugates were later incubated with 2×10⁵ OVA-specific CD8+ T cells. CTL-mediated tumor cell death was determined by decreasing luminescence activity. 2D is a bar graph depiction of tumor cell viability after treatment with protein and/or OVA-specific cytotoxic T cells (mean±SD) (Representative data of two experiments).
Figure 2B:
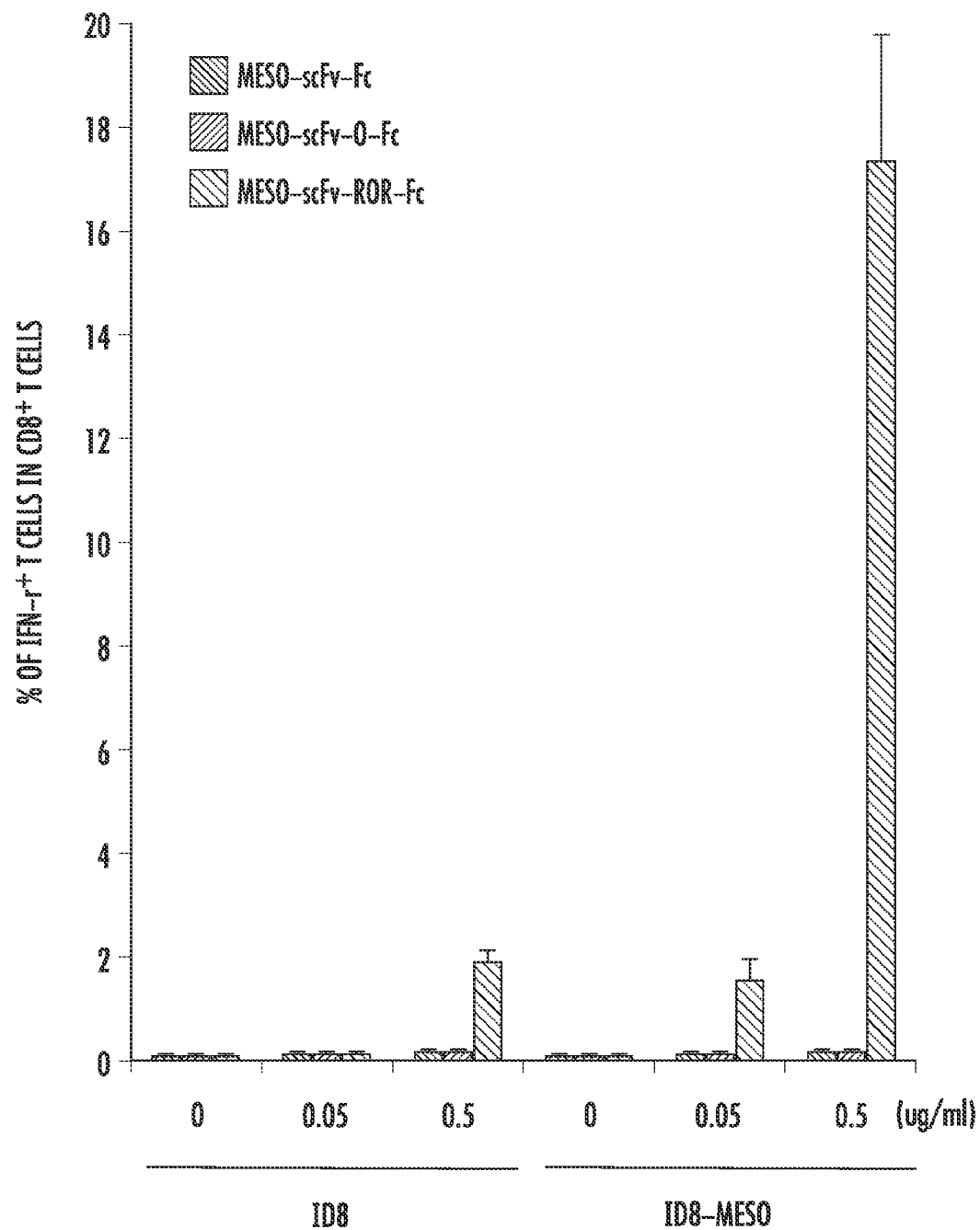

The binding of Meso-scFv-ROR-Fc to ID8-meso was investigated to determine if it could enable MHC class I presentation of OVA peptide and activate OVA-specific CD8+ T cells. As shown in FIGS. 2A, 2B, ID8-meso incubated with Meso-scFv-ROR-Fc had the greatest OVA-specific CD8+ T cell activation (>20-fold). Also, the activation of OVA-specific CD8+ T cells is positively correlated with the amount of Meso-scFv-ROR-Fc that is incubated with ID8-meso in a concentration-dependent manner. Since ID8 incubated with Meso-scFv-ROR-Fc can activate some OVA-specific CD8+ T cells, furin alone can lead to low level cleavage of the Meso-scFv-ROR-Fc protein, resulting in peptide coating of tumor cells. However, the importance of mesothelin-binding in mediating furin cleavage of chimeric protein is exemplified by the >10-fold difference in the activation of OVA-specific CTL between ID8-meso and ID8 incubated with the Meso-scFv-ROR-Fc immunoconjugate.
m Example 5

Figure 2C:
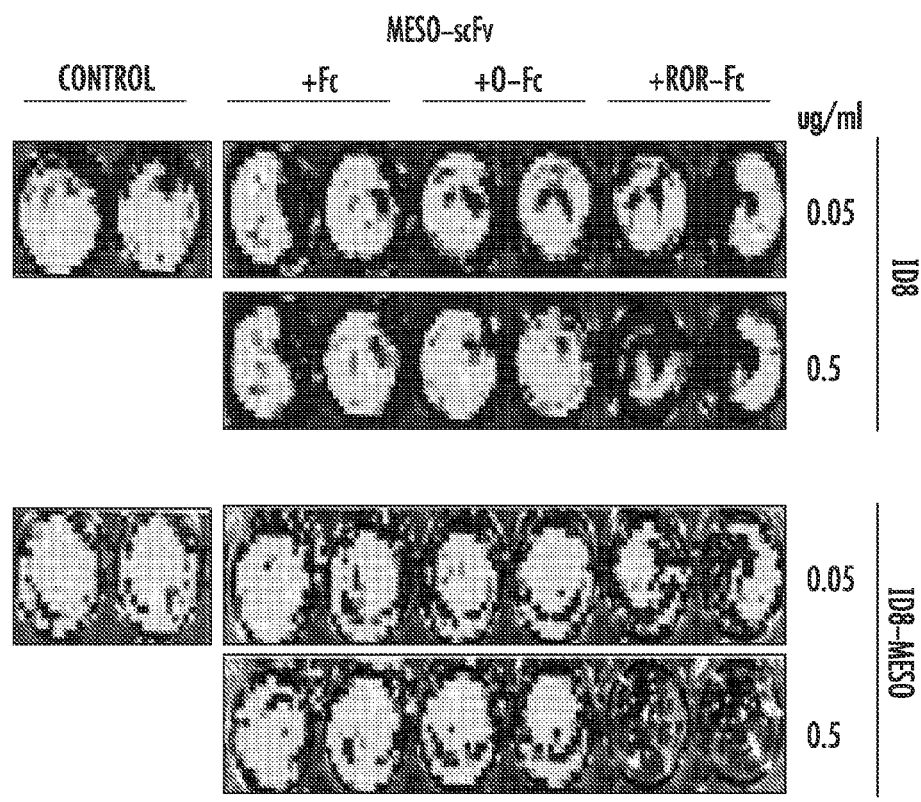
Figure 2D:
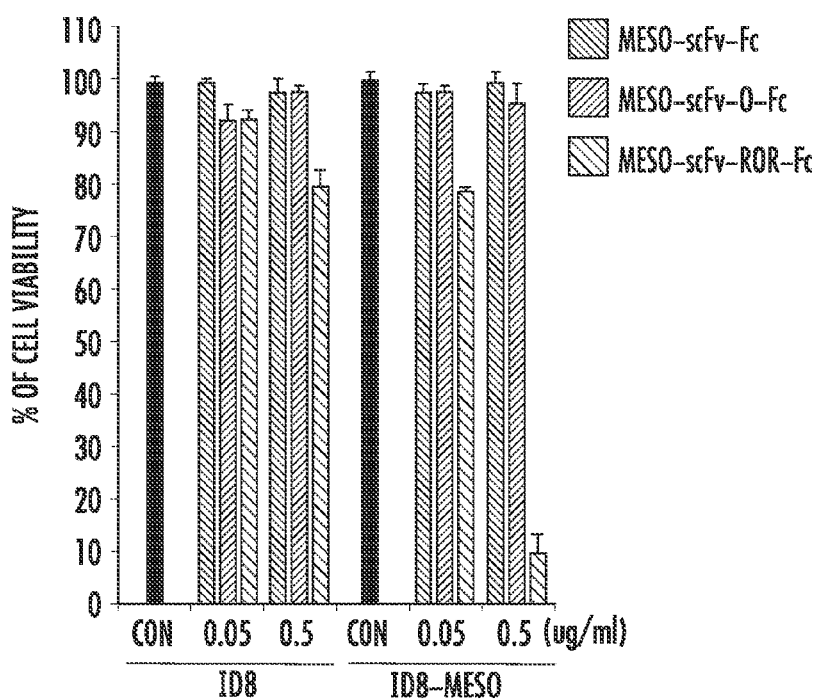

It was then determined if ID8-meso cells bound by Meso-scFv-ROR-Fc is susceptible to OVA-specific CD8+ T cell killing. As shown in FIGS. 2C, 2D, ID8-meso incubated with Meso-scFv-ROR-Fc immunoconjugate had the greatest OVA-specific CTL-mediated tumor cell death, as seen by the greatest reduction of luminescence activity. In addition, the amount of Meso-scFv-ROR-Fc incubated with ID8-meso is positively correlated with OVA-specific CTL killing of tumor cells in a dose-dependent manner. This dose-dependent killing is observed in both ID8-meso and ID8 tumor cells, though Meso-scFv-ROR-Fc binding to tumor cells increases OVA-specific CTL killing of ID8-meso (compared to ID8) by 8 fold. These results indicate Meso-scFv-ROR-Fc specifically binds ID8-meso and facilitates MHC class I presentation of OVA peptide to activate OVA-specific CD8+ T cells. Furthermore, the binding of Meso-scFv-ROR-Fc to tumor cell renders bound tumor cell susceptible to OVA-specific CTL killing.

Example 6

To determine if the immunoconjugates of the present invention can target human mesothelin-expressing ID8-meso in vivo, tumor cells from tumor-bearing mice which were i.p. injected with various Meso-scFv-Fc immunoconjugates were isolated and characterized. As shown in FIG. 3A, ID8-meso cells isolated from tumor-bearing mice injected with various immunoconjugates showed significant positive staining; indicating the immunoconjugate had bound to tumor cells. ID8-meso from mice injected with Meso-scFv-ROR-Fc had less staining while ID8-meso from mice injected with Meso-scFv-Fc and Meso-scFv-O-Fc had similarly high levels of staining. This suggests the ID8-meso from mice injected with Meso-scFv-ROR-Fc had less Fc-positive molecules due to furin-mediated loss of Fc fragment. Additionally, the reduced binding of Meso-scFv-ROR-Fc to ID8-meso (FIG. 3A) was not observed under in vitro condition (FIG. 1D) since cell binding assay was performed at 4° C., which inhibits furin function. No binding of chimeric Meso-scFv-Fc proteins to ID8 tumor cells was also observed. This suggests that the Meso-scFv portion of the immunoconjugates can specifically bind human mesothelin-expressing tumor cells, and that the furin cleavage sites flanking the OVA peptide enables the proteolytic release of Fc fragment from the immunoconjugates.

Example 7

Figure 3C:
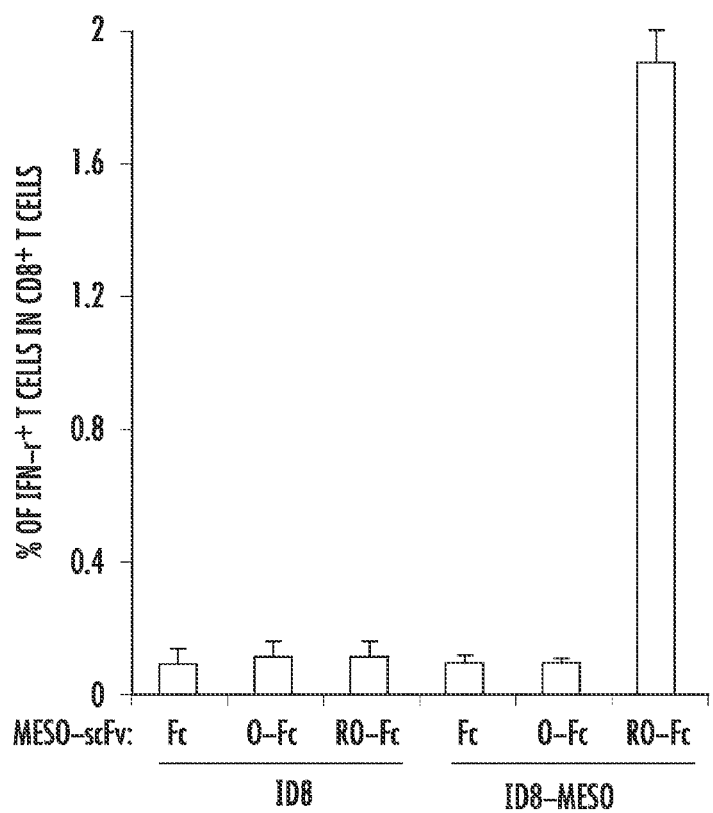

The binding of the immunoconjugates to human mesothelin-expressing ID8-meso tumor cells was then analyzed to determine if they can load OVA peptide onto MHC class I molecules and activate OVA-specific CD8+ T cells in vivo. Tumor cells isolated from the peritoneal wash of tumor-bearing mice intraperitoneally (i.p.) injected with various Meso-scFv-Fc immunoconjugates were incubated with OVA-specific CD8+ T cells. CD8+ T cell activation was characterized by intracellular cytokine staining for IFN-γ and CD8 followed by flow cytometry analysis. As shown in FIGS. 3B, 3C, tumor cells derived from the peritoneal wash of ID8-meso tumor-bearing mice i.p. injected with Meso-scFv-ROR-Fc generated the best activation of OVA-specific CD8+ T cells. In contrast, tumor cells derived from peritoneal wash of mesothelin-negative ID8 tumor-bearing mice injected with the Meso-scFv-ROR-Fc immunoconjugates led to no significant activation of OVA-specific CD8+ T cells. These data suggest that cleavage of Meso-scFv-ROR-Fc by furin in ID8-meso tumor cells can free OVA peptide to be loaded onto MHC class I molecules of ID8-meso cells and activate OVA-specific CD8+ T cells.

Example 8

Figure 4A:
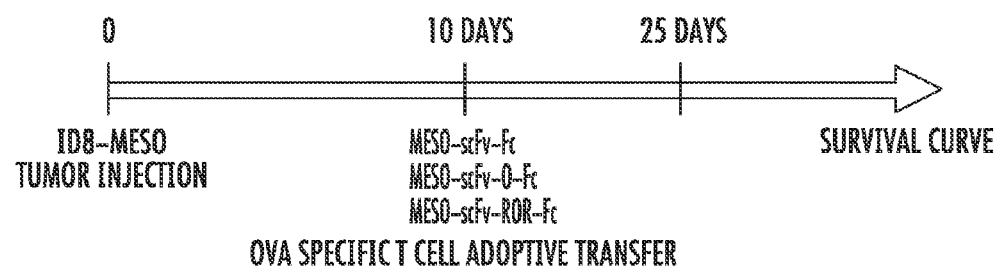
FIGS. 4A-4D show the in vivo therapeutic antitumor effects by various chimeric proteins combined with adoptive transfer of OVA-specific CD8+ T cells. 4A is a schematic diagram of the treatment regimen. Mice were i.p. injected with luciferase-expressing ID8-meso cells on day 0. On day 10, tumor-bearing mice were i.p injected with one type of immunoconjugate in conjunction with adoptive transfer of OVA-specific CD8+ T cells. Bars represent time of imaging. 4B is a representative luminescence image of fluorescence intensity (tumor load) in tumor-bearing mice treated with different immunoconjugates with or without adoptive transfer of OVA-specific CD8+ T cells. 4C is a line graph depicting the fluorescence intensity (tumor load) in tumor-bearing mice treated with different regimens. 4D is a Kaplan-Meier survival analysis of tumor-bearing mice treated with different regimens.
Figure 4B:
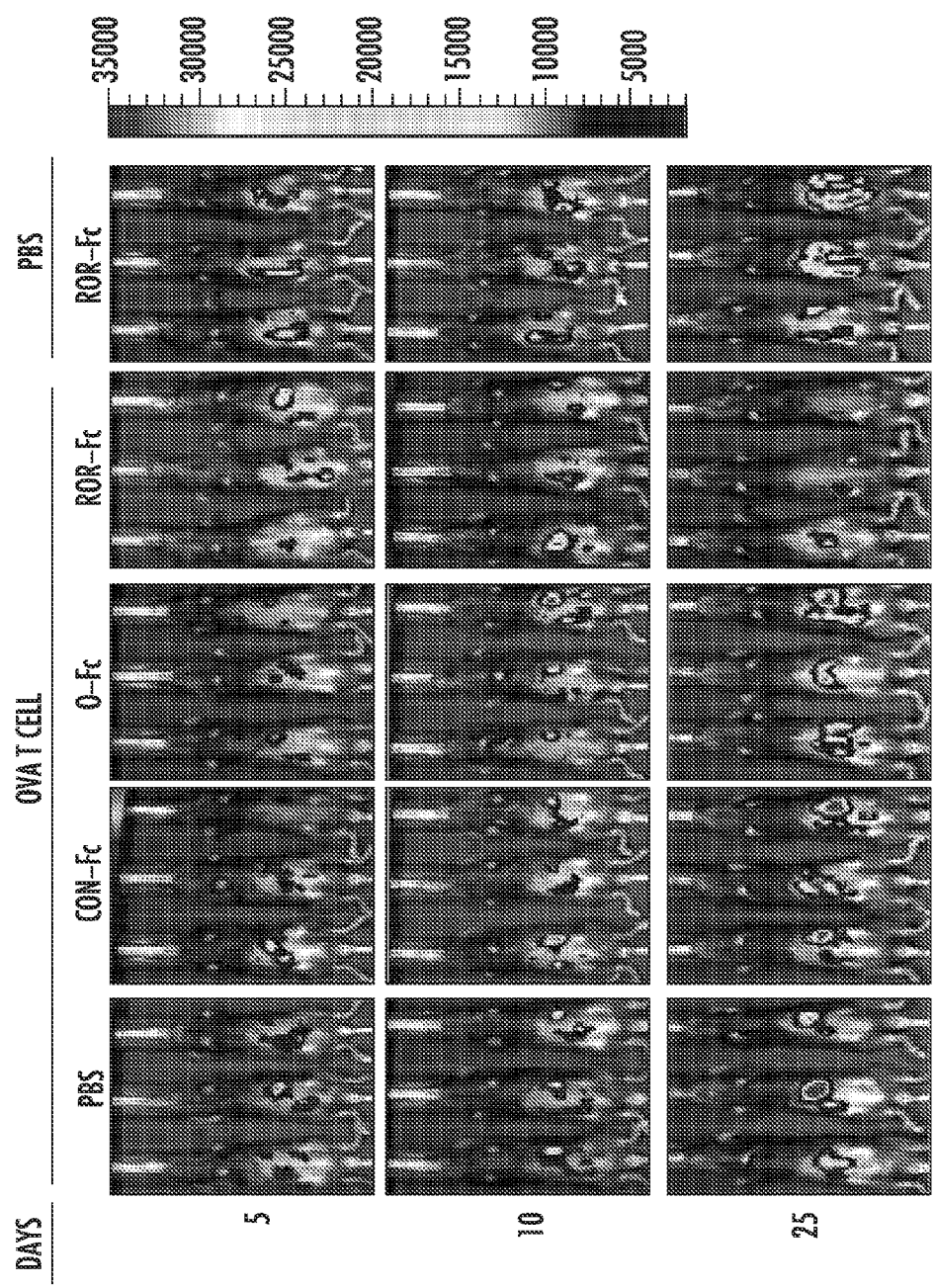
Figure 4C:
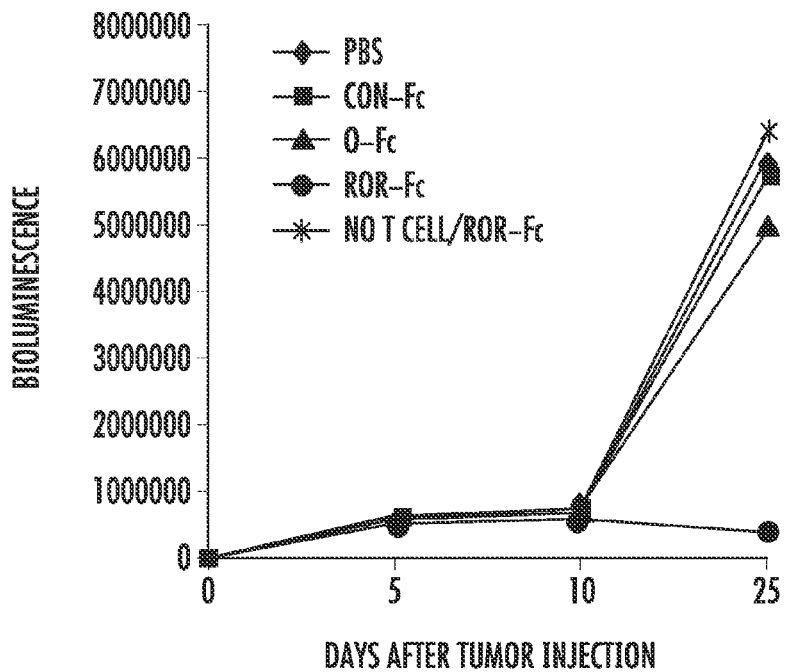
Figure 4D:
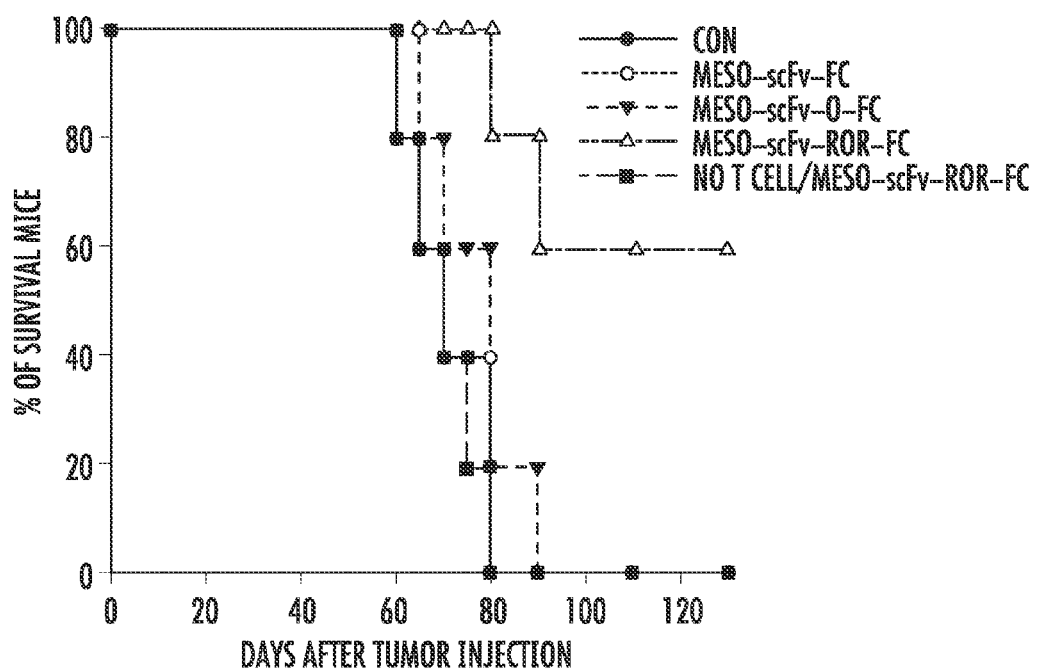

It was then determined whether i.p. administration of Meso-scFv-ROR-Fc can render human mesothelin-expressing ID8-meso tumor susceptible to OVA-specific CTL killing in vivo. FIG. 4A is a schematic diagram of the treatment regimen. As shown in FIGS. 4B, 4C, significant tumor growth reduction (decreased luminescence) was only seen in tumor-bearing mice treated with Meso-scFv-ROR-Fc in conjunction with adoptive transfer of OVA-specific CD8+ T cells. Administration of Meso-scFv-ROR-Fc without adoptive transfer elicited no therapeutic effects, suggesting anti-tumor effects are mediated by OVA-specific CD8+ T cells. Furthermore, tumor-bearing mice treated with Meso-scFv-ROR-Fc in conjunction with OVA-specific CD8+ T cells had the longest survival (FIG. 4D). This suggests that ID8-meso treated with Meso-scFv-ROR-Fc has OVA peptide-loaded MHC class I, resulting in OVA-specific CTL-mediated therapeutic antitumor effects in vivo.

Example 9

Figures 5A, 5B, 5C:
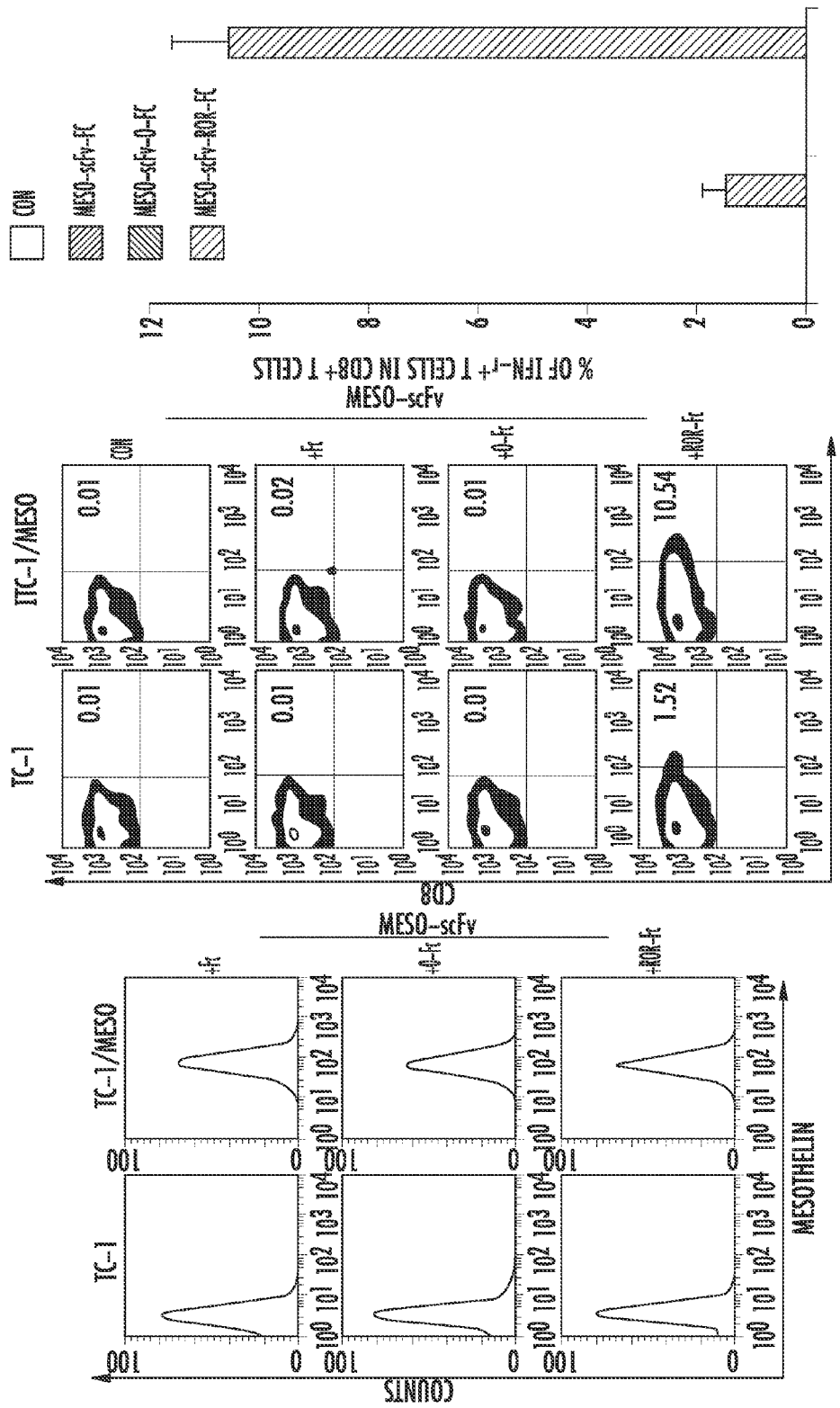
FIGS. 5A-5D show MHC class I presentation of OVA peptide to OVA-specific CD8+ T cells by TC-1/Meso tumor cells treated with Meso-scFv-ROR-Fc. 5A is a representative flow analysis of Meso-scFv-ROR-Fc protein binding to TC-1/Meso. The purified immunoconjugates were incubated with TC-1/Meso or control TC-1 tumor cells followed by staining with PE-labeled anti-mouse Fc antibody. 5B is flow cytometry characterization of OVA-specific CD8+ T cell activation by TC-1/Meso cells treated with different immunoconjugates. OVA-specific CD8+ T cell activation was determined by CD8 and intracellular IFN-γ staining. 5C is a representative bar graph depicting the % of IFN-γ-secreting OVA-specific CD8+ T cell out of total OVA-specific CD8+ T cells (mean±S.D.). 5D shows representative luminescence imaging of in vitro OVA-specific CTL killing of luciferase-expressing TC-1/Meso cells treated with Meso-scFv-ROR-Fc immunoconjugate. The degree of CTL-mediated tumor cell death is indicated by decrease of luminescence activity. 5E is a bar graph depicting viability of tumor cells treated with protein and/or OVA-specific cytotoxic T cells (mean±S.D.) (Representative data of two experiments).
Figures 5D, 5E:
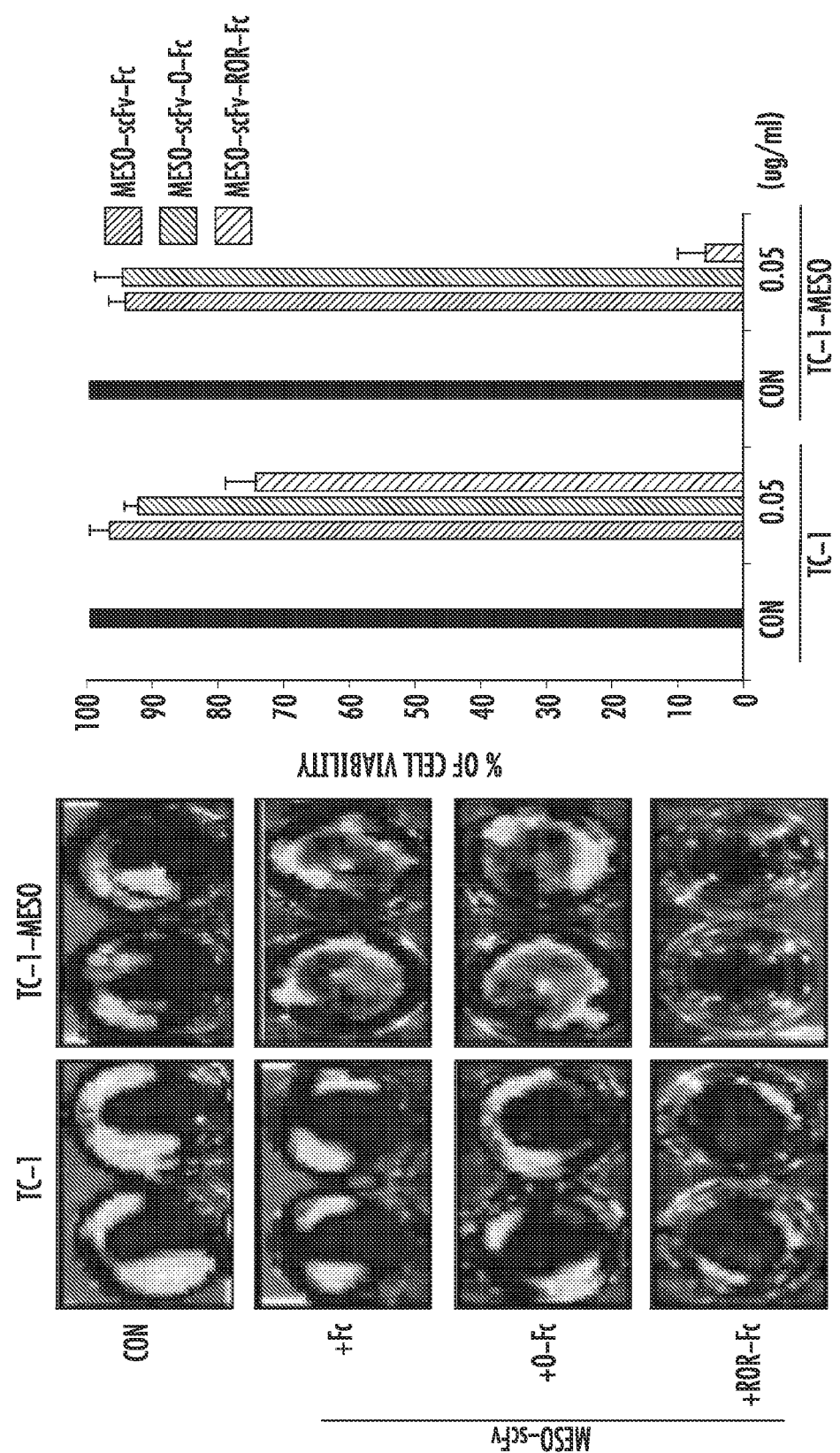

The immunoconjugates of the present invention were then tested in another human mesothelin-expressing murine tumor cell line, TC-1/Meso. TC-1/Meso incubated with the various Meso-scFv-Fc proteins stained positive for cell binding, unlike mesothelin-negative TC-1 cells (FIG. 5A). Additionally, TC-1/Meso incubated with Meso-scFv-ROR-Fc had the best activation of OVA-specific CD8+ T cells (FIGS. 5B, 5C). However, mesothelin-negative TC-1 incubated with Meso-scFv-ROR-Fc activated OVA-specific CD8+ T cells to a small degree. This suggests some of the Meso-scFv-ROR-Fc may have been cleaved by the furin expressed in TC-1, leading to the loading of OVA peptides on the MHC class I molecules and activation of OVA-specific CD8+ T cells. Like the ID8-meso tumor system, the OVA-specific CD8+ T cell activation by mesothelin-negative TC-1 is (~7 fold) lower than that of mesothelin-positive TC-1/Meso. As shown in FIGS. 5D, 5E, Meso-scFv-ROR-Fc binding to TC-1/Meso led to the greatest OVA-specific CTL-mediated tumor cell death. Low level tumor killing was also observed in TC-1 tumor cells pulsed with Meso-scFv-ROR-Fc compared to TC-1/Meso (~15 fold difference). The data demonstrates that the present invention works in another mesothelin-expressing tumor model, TC-1/Meso.

Example 10

Figure 6B:
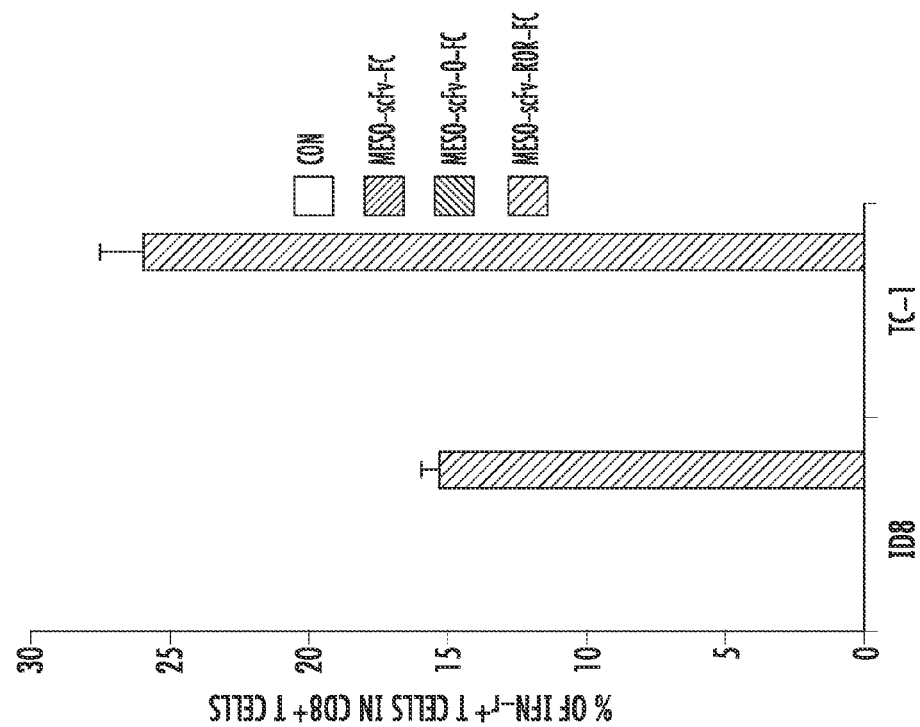
FIGS. 6A-6D depict MHC Class I presentation of ova peptide by mesothelin-negative tumor cells following incubation with supernatant from ID8-meso or TC-1/Meso treated with Meso-scFv-ROR-Fc immunoconjugates. 6A is flow cytometry characterization of OVA-specific CD8+ T cell activation by ID8 or TC-1 tumor cells incubated with supernatant of ID8-meso or TC-1/Meso cells treated with different immunoconjugates. After supernatant treatment, OVA-specific CD8+ T cells were added to ID8 or TC-1 cells. OVA-specific CD8+ T cell activation was determined by IFN-γ and CD8 staining 6B is a bar graph depicting the % of IFN-γ-secreting OVA-specific CD8+ T cells out of total OVA-specific CD8+ T cells (mean±S.D.). 6C is representative luminescence imaging of in vitro OVA-specific CTL killing of luciferase-expressing ID8 or TC-1 cells incubated with supernatant from ID8-meso or TC-1/Meso tumor cells treated with Meso-scFv-ROR-Fc immunoconjugate. The killing of luciferase-expressing ID8 or TC-1 tumor cells was detected by decreased luminescence activity. 6D is a bar graph depicting viability of ID8 or TC-1 tumor cells after incubation with supernatant from ID8-meso or TC-1/Meso cells treated with protein and/or OVA-specific cytotoxic T cells (mean±S.D.) (Representative data of two experiments).
Figure 6A:
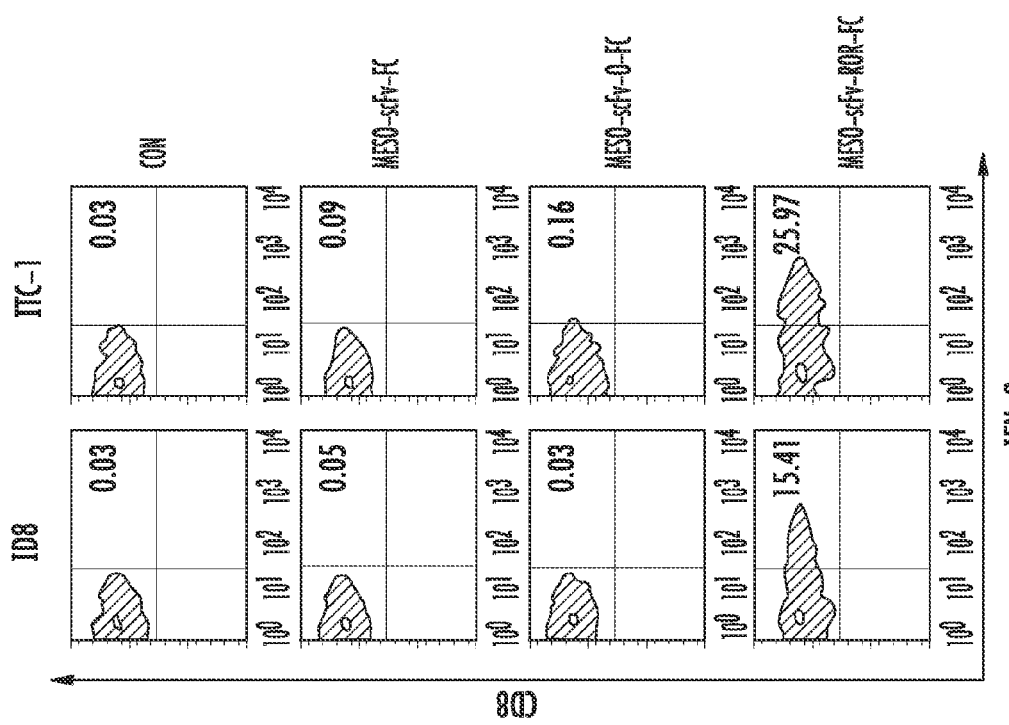
Figure 6D:
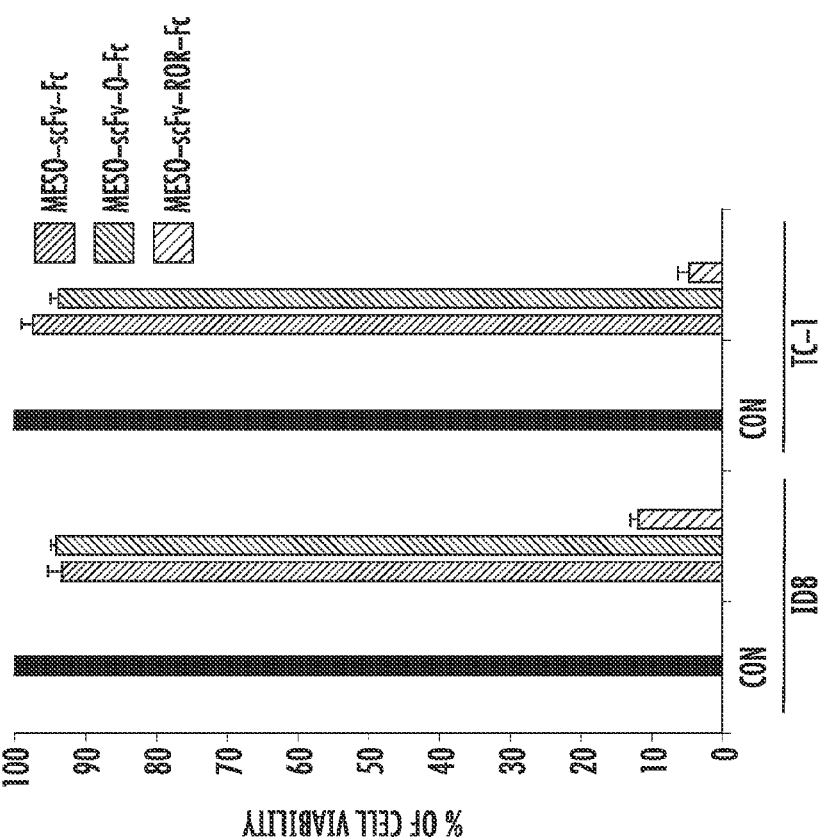
Figure 6C:
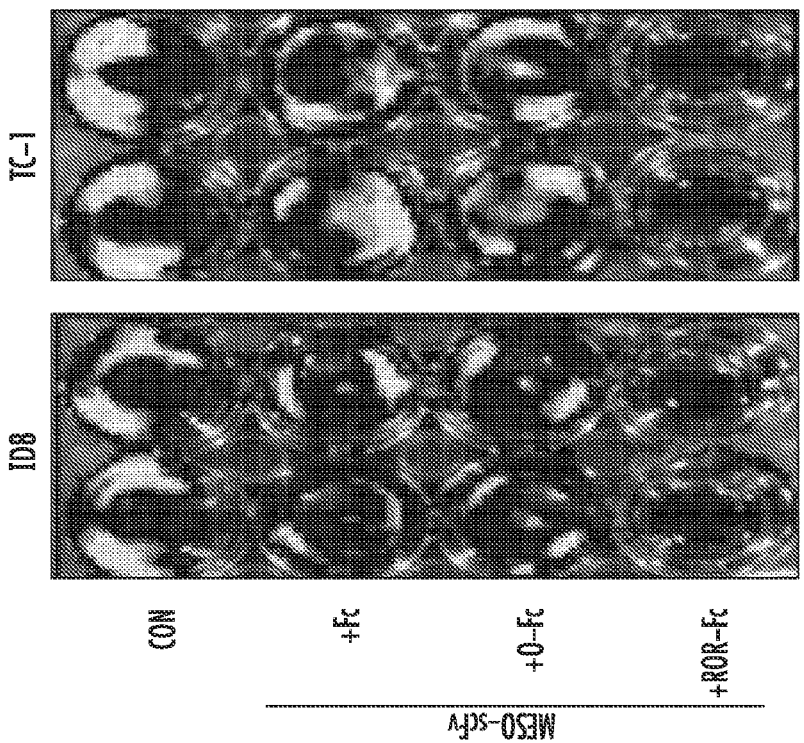
Figure 7B:
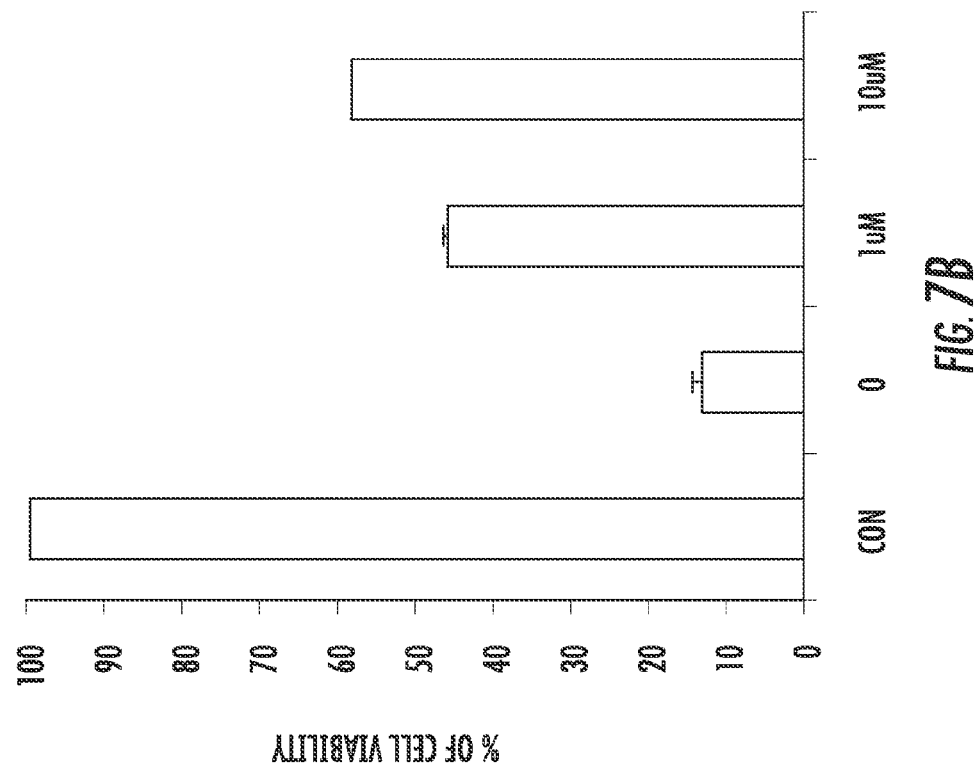
FIGS. 7A-7B show that furin facilitates the coating of tumor cells with antigenic peptides. 7A depicts representative luminescence imaging of in vitro OVA-specific CTL killing of luciferase-expressing ID8-meso cells treated with 0, 1, or 10 μM of furin inhibitor (calbiochem) and Meso-scFv-ROR-Fc. Treated tumor cells were incubated with 2×10⁵ OVA-specific CD8+ T cells. The degree of CTL-mediated tumor cell death was indicated by decrease in luminescence activity. 7B is a bar graph depicting viability of tumor cells treated with protein and/or OVA-specific CD8+ T cells (mean±S.D.) (Representative data of two experiments).
Figure 7A:
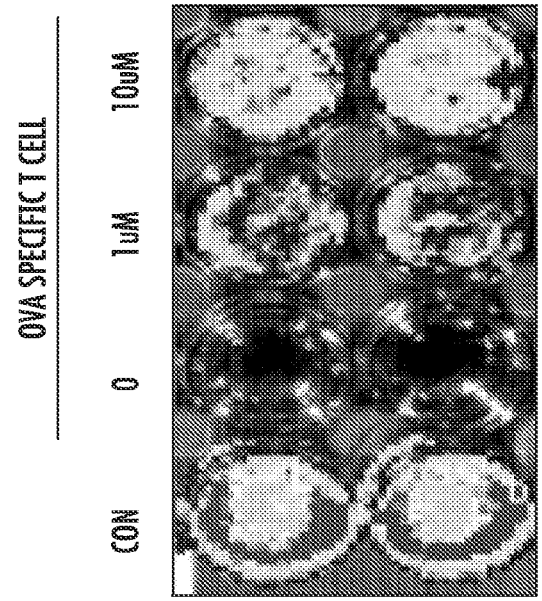

The question of whether the release of OVA peptide by furin cleavage of Meso-scFv-ROR-Fc in bound tumor cells can also make mesothelin-negative non-bound tumor cells targets of OVA-specific CTL-mediated killing was then investigated. The supernatants from ID8-meso or TC-1/Meso tumor cells treated with different Meso-scFv-Fc immunoconjugates were collected and incubated with mesothelin-negative ID8 and TC-1 tumor cells. OVA-specific CD8+ T cells were then added and activation was analyzed by intracellular cytokine staining for IFN-γ and CD8 followed by flow cytometry analysis. As shown in FIGS. 6A, 6B, only the supernatant from ID8-meso or TC-1/Meso cells treated with Meso-scFv-ROR-Fc could activate OVA-specific CD8+ T cells upon incubation with mesothelin-negative ID8 or TC-1 cells. Furthermore, as shown in FIGS. 6C, 6D, luciferase-expressing ID8 or TC-1 tumor cells that were incubated with supernatant from ID8-meso or TC-1/Meso tumor cells treated with Meso-scFv-ROR-Fc had the greatest tumor cell death (reduced luminescence) upon addition of OVA-specific CD8+ T cells. Also, the furin inhibitor experiment suggests the importance of furin in releasing OVA peptide for loading of MHC class I molecules (FIGS. 7A, 7B). These findings suggest that the specific binding of Meso-scFv-ROR-Fc to human mesothelin-expressing tumors can lead to the release of OVA peptide and sensitize non-bound tumor cells to OVA-specific CTL-mediated killing.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An immunoconjugate having the formula:

$$T\text{-}c\text{-}Fc_n\text{-}c\text{-}E_n;$$

wherein

T is a single chain variable portion fragment of a monoclonal antibody (scFv) directed to a target protein, polypeptide, or fragment thereof, which is highly expressed on cancer cells, and selected from the group consisting of scFv directed to mesothelin, epidermal growth factor receptor (EGFR), NKG2D, or Her2/neu protein;

$E_n$ is two or more foreign immunogenic CD8+ T cell antigenic epitopes derived from ovalbumin, Epstein-Barr virus, cytomegalovirus, human papilloma virus, and influenza wherein n is 1 to 10;

c is a peptide or polypeptide fragment thereof, capable of being cleaved by by furin, MMP1 or MMP9; and $Fc_n$ is two or more Fc portions of an IgG antibody wherein n is 1 to 10.

2. The immunoconjugate of claim 1, wherein c is a furin cleavable peptide having the amino acid sequence RVKR (SEQ ID NO: 2).

3. The immunoconjugate of claim 1, wherein E is an ovalbumin epitope having the amino acid sequence SIINFEKL (SEQ ID NO: 1).

4. The immunoconjugate of claim 1, wherein T is a scFv directed to mesothelin.

5. A method for making a tumor cell susceptible to $CD8^+$ T cell killing, comprising determining whether the $CD8^+$ T cell antigenic epitopes is specific for an antigen presented on the tumor cell and then contacting one or more tumor cells with the immunoconjugate of claim 1 having said antigenic epitope.

* * * * *

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: synthetic sequence

<400> SEQUENCE: 1

Ser Ile Ile Asn Phe Glu Lys Leu
1               5

<210> SEQ ID NO 2
<211> LENGTH: 4
<212> TYPE: PRT
<213> ORGANISM: Artificial Sequence
<220> FEATURE:
<223> OTHER INFORMATION: synthetic sequence

<400> SEQUENCE: 2

Arg Val Lys Arg
1
```